(12) United States Patent
Geddes

(10) Patent No.: US 9,162,016 B2
(45) Date of Patent: Oct. 20, 2015

(54) BREASTPUMP WITH IRREGULAR MILK EXPRESSION SEQUENCES

(75) Inventor: Donna T. Geddes, Dianella, WA (US)

(73) Assignee: Medela Holding AG, Baar (CH)

( * ) Notice: Subject to any disclaimer, the term of this patent is extended or adjusted under 35 U.S.C. 154(b) by 1458 days.

(21) Appl. No.: 11/903,103

(22) Filed: Sep. 20, 2007

(65) Prior Publication Data

US 2008/0097290 A1   Apr. 24, 2008

Related U.S. Application Data

(60) Provisional application No. 60/846,689, filed on Sep. 22, 2006.

(51) Int. Cl.
*A61M 1/06* (2006.01)
*A61M 1/00* (2006.01)

(52) U.S. Cl.
CPC ............... *A61M 1/06* (2013.01); *A61M 1/0037* (2013.01)

(58) Field of Classification Search
CPC ............................. A61M 1/06; A61M 1/0037
USPC ................ 604/73, 74, 313; 119/14.01, 14.02
See application file for complete search history.

(56) References Cited

U.S. PATENT DOCUMENTS

| | | | |
|---|---|---|---|
| 4,213,457 A | 7/1980 | Lewis | |
| 4,315,506 A | 2/1982 | Kayser et al. | |
| 4,794,915 A | 1/1989 | Larsson | |
| 4,857,051 A | 8/1989 | Larsson | |
| 4,964,851 A | 10/1990 | Larsson et al. | |
| 5,007,899 A | 4/1991 | Larsson et al. | |
| 5,218,924 A * | 6/1993 | Thompson et al. | ........ 119/14.02 |
| 5,947,923 A | 9/1999 | Uehara et al. | |
| 6,045,529 A | 4/2000 | Neesch | |
| 6,383,163 B1 | 5/2002 | Kelly et al. | |
| 6,497,677 B2 | 12/2002 | Silver et al. | |
| 6,547,756 B1 | 4/2003 | Greter et al. | |
| 6,699,213 B1 | 3/2004 | Annis et al. | |
| 7,727,182 B2 | 6/2010 | Silver | |
| 2002/0193731 A1 | 12/2002 | Myers et al. | |
| 2004/0024351 A1 | 2/2004 | Greter et al. | |
| 2005/0043677 A1* | 2/2005 | Kelly et al. | ..................... 604/74 |
| 2005/0228342 A1 | 10/2005 | Yuen | |
| 2005/0234370 A1 | 10/2005 | Beal et al. | |
| 2006/0052746 A1 | 3/2006 | Liao | |

FOREIGN PATENT DOCUMENTS

| | | |
|---|---|---|
| CA | 2530726 A1 | 6/2006 |
| EP | 1468705 A2 | 10/2004 |
| JP | 07-136245 | 5/1995 |

(Continued)

OTHER PUBLICATIONS

Kent. J.C. et al., "Response of Breasts to Different Stimulation Patterns of an Electric Breast Pump". Journal of Human Lactation, vol. 19, No. 2, pp. 179-186, 2003.*
Mitoulas, L.R. et al. "Efficacy of Breast Milk Expression Using an Electric Breast Pump" Journal of Human Lactation, vol. 18, No. 4, pp. 344-352, 2002. See whole document.
Mitoulas, L.R. et al. "Effect of Vacuum Profile on Breast Milk Expression Using an Electric Breast Pump." Journal of Human Lactation, vol. 18. pp. 353-360. See whole document.

(Continued)

*Primary Examiner* — Theodore Stigell
(74) *Attorney, Agent, or Firm* — McDonnell Boehnen Hulbert & Berghoff LLP

(57) ABSTRACT

The present invention is directed to a breastpump that can be operated to generate milk expression sequences or curves with some irregularity or randomness in the course of a session.

18 Claims, 7 Drawing Sheets

(56) References Cited

FOREIGN PATENT DOCUMENTS

| | | |
|---|---|---|
| JP | 09-066099 | 3/1997 |
| WO | WO0147577 A2 | 7/2001 |
| WO | WO2005/016409 | 2/2005 |

OTHER PUBLICATIONS

International Search Report for Application PCT/AU2007/001402 issued Nov. 8, 2007.
International Search Report for Application PCT/AU2007/001401 issued Oct. 30, 2007.

* cited by examiner

BREASTPUMP WITH IRREGULAR MILK EXPRESSION SEQUENCES

HISTORY

Applicant claims the benefit of U.S. Provisional Application Ser. No. 60/846,689 filed on Sep. 22, 2006, entitled "Infant Sucking and the Effect of Respiration and Swallowing: Shapes, Patterns and Vacuum in Depth Including Frequency, Vacuum and Breast Expression."

BACKGROUND

1. Field of the Application

The invention relates generally to breastpumps for drawing breastmilk, and particularly to a new way to operate a breastpump, such as a motorized, electrically driven breastpump, to better simulate an infant during breastfeeding.

2. Description of the Related Art

Breastpumps for use by nursing mothers are well known. They allow the nursing woman to express the breastmilk as necessary or convenient, and further provide collection of the breastmilk for later use. For some mothers, breastpumps may be a necessity, such as when the mother is away from the child (as at work), the child has suckling problems, or if the mother has problems with excessive or deficient milk production, or soreness, deformation or injury of the mammilla.

Historically, electrically driven motorized breastpumps have been made with a single type of "cycle" for a given pump. That is, the driving mechanism for generating the vacuum (negative pressure) to be applied at the breast is geared to a particular sequence, or curve, of negative pressure increase (i.e., increasing suction), and then release. This is often aimed at reproducing in some sense the suckling action of an infant, for instance. Breastpumping can cover a range of different conditions, however, such as where the mother's nipples are sore for some reason, there is a state of significant engorgement, some nipple stimulation may be particularly desired, let-down and relaxation may be of particular interest, it may be desired to increase milk production, and so on.

Some breastpumps have provided the user with the ability to vary the amount of peak vacuum being applied, as well as the speed of the pumping action (i.e., number of cycles per minute, or frequency). The basic "curve" or sequence remains fixed, however, and the user must adapt as best she can to making variations within that particular curve built into the machine, which typically has been generalized for the overall population of users. FIG. 1 shows such a prior art sequence that yields a simple smooth curve between a maximum vacuum and ambient conditions (negative pressure is along the y-axis (in millimeters of mercury) and time (in seconds) along the x-axis). Note how the cycle depicted repeats itself (here, every 1.25 seconds).

The SYMPHONY breastpump by Medela, Inc., which is the subject matter of U.S. Pat. No. 6,547,756, introduced both a breastpump that can be programmed to generate a plurality of differing milk expression sequences or curves, as well as the ability to now generate a sequence that had special inflections, or modifications, that differed from a smooth curve. In FIG. 2, which is the Superior program, note how the maximum negative pressure peak ($P_1$) is followed by a slight pause ($P_2$), thereby yielding a curve shape that is different from that of the standard curve of FIG. 1. Although providing a number of choices for the mother in the way of different shaped curves, each of these programs is predictable and regular, i.e., the cycle or sequence repeats itself (at least while that particular sequence is in operation, since a plurality of different sequences may be used in a session, e.g., letdown, then an expression sequence.

This type of regularity, however, is not presented by an infant when breastfeeding. During breastfeeding, an infant does not suck in a regular repeatable pattern, but rather pauses at times, and may further change the level of force applied (e.g., suction) and even the rate in rapid fashion. It is therefore the consideration of this invention to better simulate an infant during breastfeeding by providing a breastpump that can be operated to generate milk expression sequences or curves with some irregularity or randomness therein.

SUMMARY OF THE INVENTION

The present invention variously meets these foregoing objectives, and more, by providing a breastpump that can be operated, as by being programmed, to generate milk expression sequences or curves with some irregularity or randomness in the functioning of the same. That is, the pattern of sequences or curves is not simply a repetition of a particular sequence or curve.

These as well as other aspects and advantages of the invention will become further apparent to those of skill in the art by reading the following detailed description, with reference where appropriate to the accompanying drawings. Further, it should be understood that the embodiments described herein are intended to illustrate the invention by way of example only.

BRIEF DESCRIPTION OF THE DRAWINGS

Exemplary embodiments of the invention are described herein with reference to the drawings, in which.

DETAILED DESCRIPTION OF EMBODIMENTS OF THE INVENTION

The present invention may be implemented on a breastpump that can be programmed to generate a plurality of differing milk expression (extraction) sequences or curves. One such breastpump is the SYMPHONY breastpump by Medela, Inc., which is the subject matter of U.S. Pat. No. 6,547,756, hereby incorporated by reference. The invention is considered to have broader application beyond a so-called programmable breastpump, however. For example, it is envisioned that an electrically operated pump could be provided with a mechanism that is not controlled by a CPU (i.e., computer programmed), yet would still cause the pump to function with some randomness in the sequences generated, as by the use of gearing, circuitry or the like.

In the embodiment described specifically hereafter, the breastpump utilizes a microprocessor-based system that is provided with user input through a plurality of "chip" cards. Each chip card contains one or more predetermined programs recorded on an EEPROM. For example, each card could contain a specific type of sequence.

It will be readily understood that a chip card is but one way to program the microprocessor. Other input means could be used, such as dedicated buttons, each set to actuate a given sequence pre-programmed into the microprocessor. A numeric pad could be provided to input a code. The programs could be provided through an electronic data link, such as a modem, or optically, or otherwise.

Figure 1:
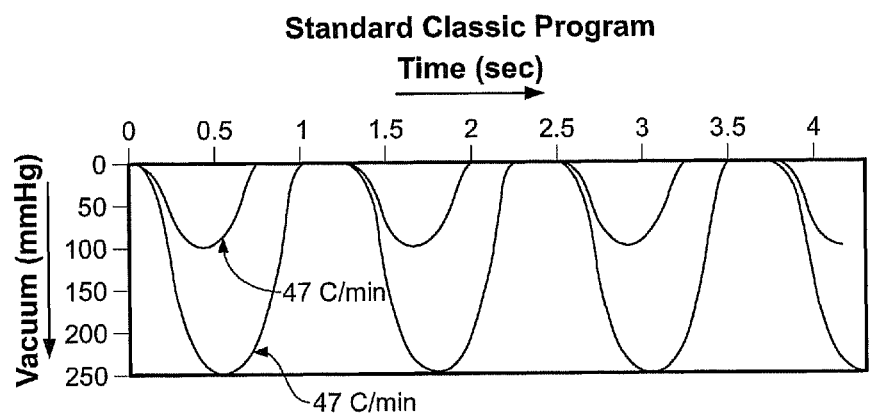
FIGS. 1 and 2 are various prior art methods (curves) for operating a breastpump.
Figure 2:
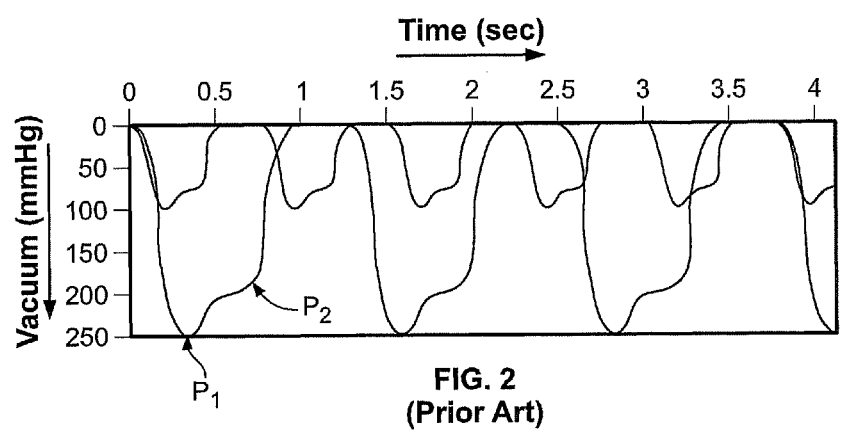

There may also be a combination of a certain programmed input of a special curve as a discrete repeating sequence (such as the foregoing Superior curve of FIG. 2), with another input or mechanism that then adjusts that curve with the randomness or irregularity of this invention.

To create non-regular milk expression sequences or curves, variability and randomness may be added to one or more of the characteristics of curves/sequences in the session. There could be a variation in: duration; number of vacuum peaks; grouping of peaks; pauses (number, place and time of each); peak vacuums; baseline vacuums; and frequency.

Figure 3:
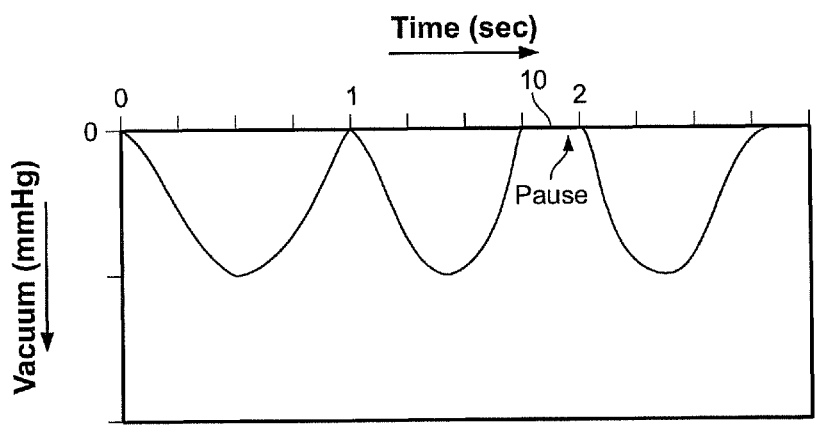
FIGS. 3 through 9 are exemplary methods (curves) for operating a breastpump in accordance with the present invention.
Figure 4:
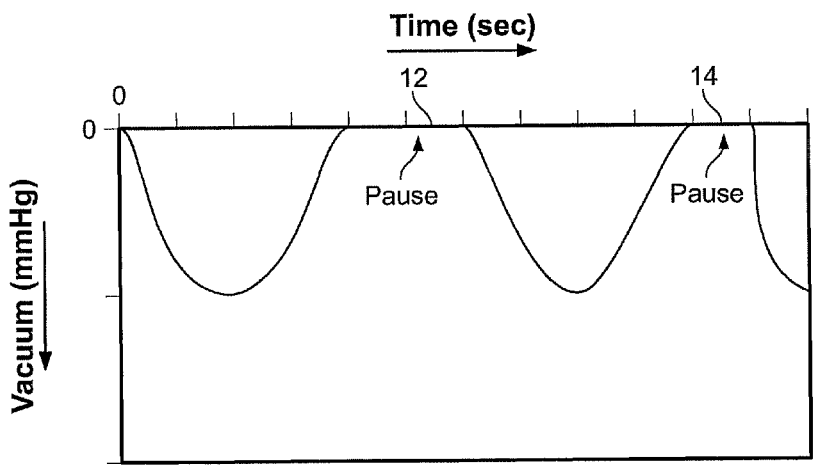

Thus, non-regularity may be added to a curve by introducing pauses at different instances in the cycle, or varying the length of the pauses, as seen in FIGS. 3 and 4. It can be seen that a pause 10 has been inserted in the otherwise regularly repeating pattern of FIG. 3. That pause would not necessarily be repeated after the next two peaks, but perhaps after the third or subsequent peak thereafter, so as to occur at different times in the cycle. It is to be noted that the pauses 12, 14 of FIG. 4 differ in duration. So, it is contemplated that pauses can be added to the curve randomly, the occurrence of each pause to be determined by a random generator, for instance.

Figure 5:
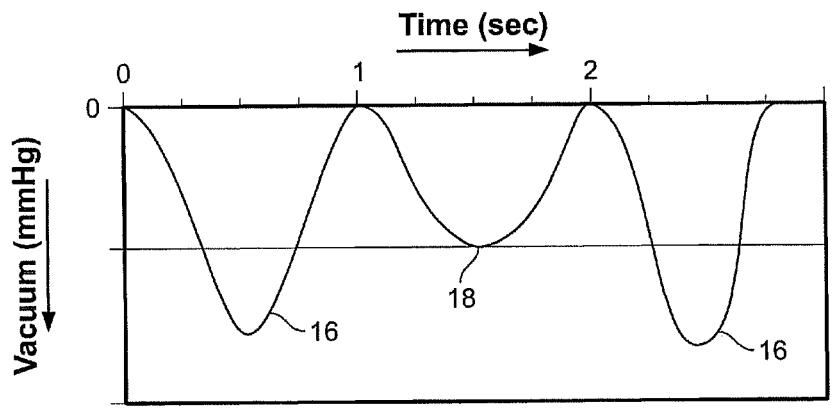
Figure 6:
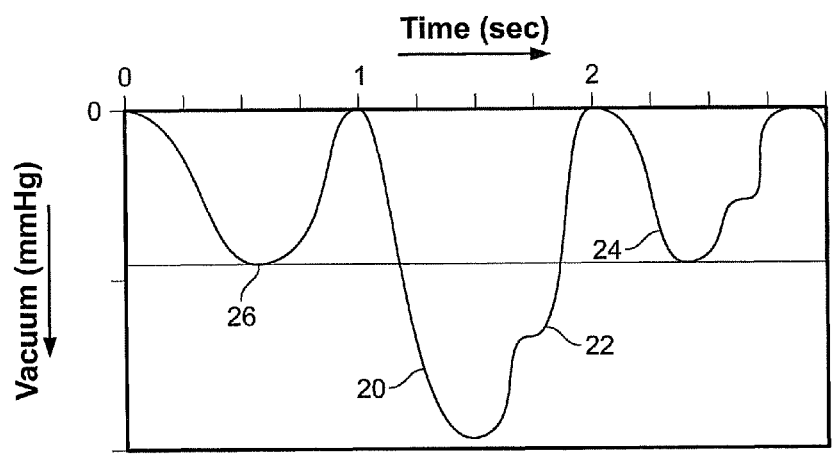

Non-regularity may be added by varying the maximum (peak) vacuum, as seen in FIG. 5. That peak vacuum may be varied over multiple different peaks, or for instance by varying the timing of the two peak vacuums illustrated in FIG. 5 (e.g., peak vacuum 16 may appear at irregular times in a sequence, perhaps with multiple lower peak vacuums 18 in between). As can be seen in the cycle of FIG. 6, the maximum vacuum peak 20 has been provided with an inflection (pause) 22, as has peak 24, while peak 26 is in a smooth curve.

Figure 7:
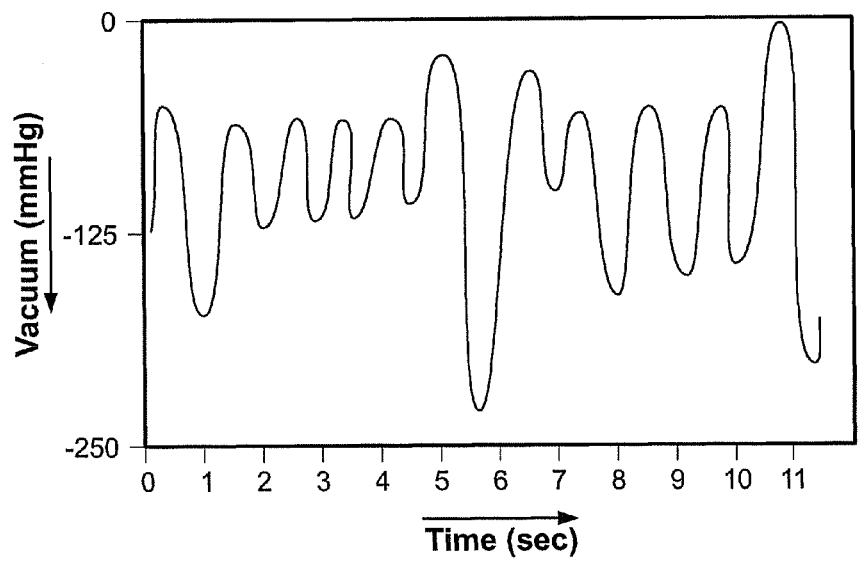

FIG. 7 illustrates how a variety of different vacuum peaks may be associated in a pumping session, here also using a baseline vacuum during portions of that session; the baseline vacuum is indicated where the curves do not return to ambient (zero, i.e., no negative pressure).

Figure 8:
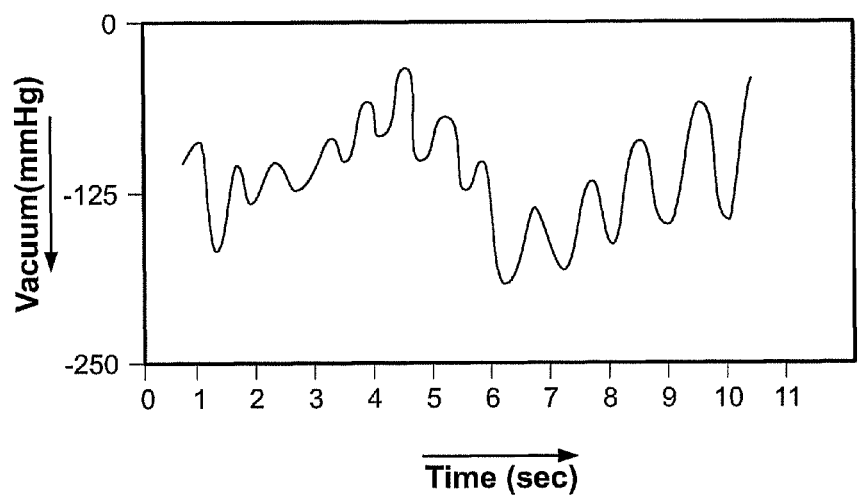

FIG. 8 shows an irregular pattern for peak vacuums as well as time duration of a given curve in the pattern for the session. In this pattern, there is also a somewhat graduated decrease in the peak vacuums in the beginning of the illustrated pattern, then a gradual increase in peak negative pressures, followed by a different graduated decrease in the same.

Figure 9:
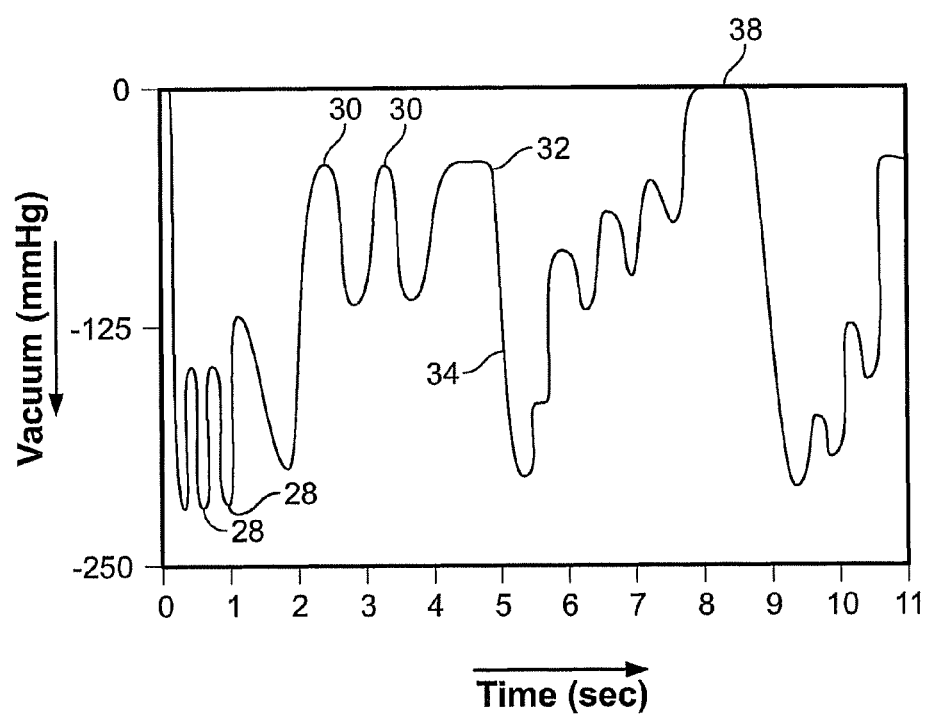

FIG. 9 illustrates a pattern for part of a session characterized by a somewhat staccato group of higher vacuum curves 28, followed by some decreasing but longer frequency curves (some (e.g., 30) at a baseline vacuum) with a pause thrown in at 32, followed by a non-smooth curve 34, then a series of gradually decreasing peak vacuums, with a pause 38 at ambient, then back up to a peak vacuum, and so forth.

Figure 10:
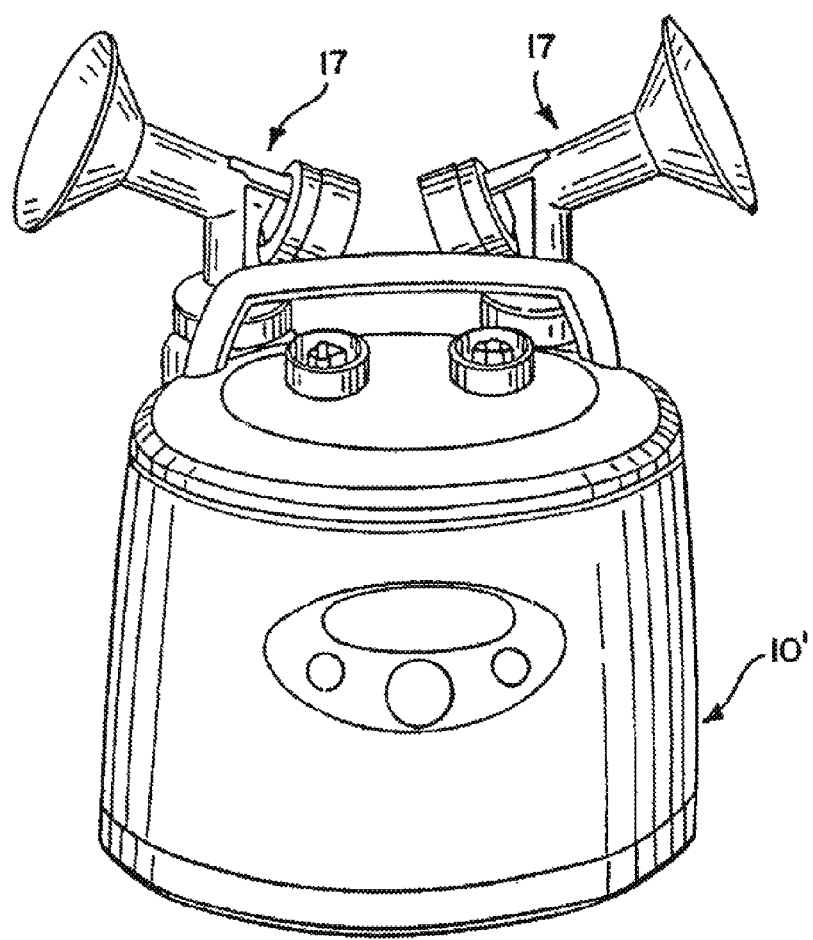
FIGS. 10 and 11 depict an exemplary breastpump with which the present invention may be used.
Figure 11:
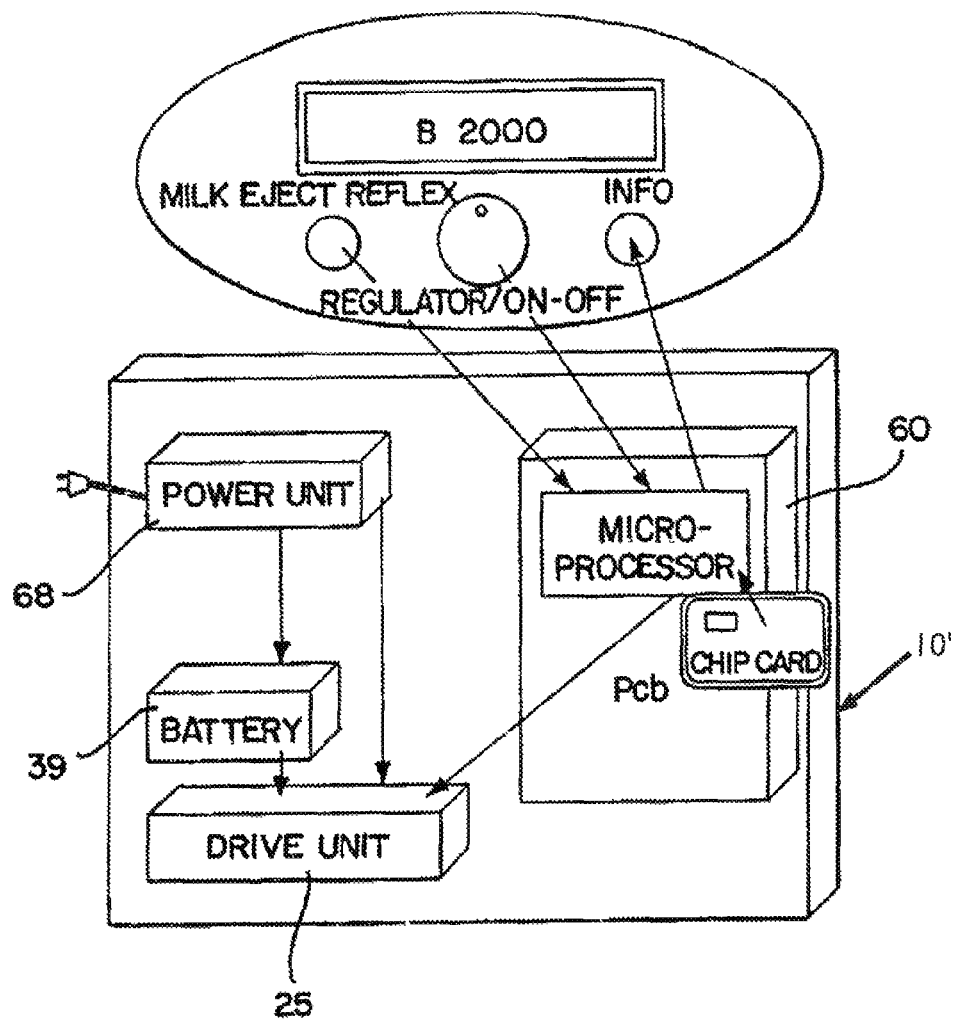

FIG. 10 depicts the exterior of an exemplary breastpump 10 with which the present invention may be used. The breastpump 10' includes breastshields 17. As seen in FIG. 11, the breastpump 10' further includes a drive unit 25 and microprocessor 60. Microprocessor 60 is integrated with the drive unit 25 to effect operation of the drive unit in accordance with the selected program, drawing upon either the AC power source as converted via standard technology to DC (indicated at 68), or from the battery source 39.

It will be understood that while these foregoing illustrated methods in the Figures show a timeline beginning at zero, these patterns could just as readily appear in the course of a session (which would last much longer than just the indicated approximately ten seconds of these charts). It will be further understood that the irregular or random nature of the patterns of this invention need not be completely non-repeating throughout an expression session. That is, a pattern of curves/sequences with irregularity/randomness therein may itself repeat (as a pattern) during the session. The point here is that there is some significant irregularity in the curves being generated, which will be felt by the mother, and which would be more than simply switching from one type of sequence (as for letdown) to another (as for expression after letdown). The mother should perceive that the expression part of the session has some non-uniformity in the sequences or cycles in accordance with the invention.

While certain features and embodiments of the present application have been described in detail herein, it is to be understood that the application encompasses all modifications and enhancements within the scope and spirit of the following claims.

What is claimed is:

1. A breastpump comprising:
   a breastshield having a portion within which a woman's breast and nipple are received for expressing milk;
   a source of pressure in communication with said breastshield for manipulating the breast and nipple to express milk;
   a predetermined program for operating the source of pressure according to a sequence that yields a non-regular pattern of pumping cycles;
   a controller which operates the source of pressure according to said program; and
   a random generator;
   wherein the non-regular pattern comprises an occurrence of a pause to be determined by the random generator at generally random intervals in the pattern.

2. The breastpump of claim 1 wherein the non-regular pattern comprises a duration of the pause in the sequences, with a plurality of such pauses of differing duration.

3. The breastpump of claim 1 wherein the non-regular pattern comprises a plurality of differing maximum vacuums in the pattern.

4. The breastpump of claim 1 wherein said non-regular pattern repeats itself throughout a pumping session.

5. The breastpump of claim 1 wherein the source of pressure is a source of vacuum.

6. A method for operating a breastpump, the breastpump comprising:
   a breastshield having a portion within which a woman's breast is received for expressing milk;
   a source of pressure in communication with the breast shield for manipulating the breast and nipple to express milk; a controller; and a random generator, wherein the controller operates the source of pressure according to sequences that yield a non-regular pattern of pumping cycles wherein the non-regular pattern comprises the occurrence of a pause at generally random intervals in the pattern, wherein the random generator determines the occurrence of the pause in the pattern.

7. The method of claim 6 wherein the non-regular pattern includes an occurrence of the pause between consecutive pluralities of sequences during said pattern.

8. The method of claim 6 wherein the non-regular pattern includes varying duration pauses in the pattern.

9. The method of claim 6 wherein the non-regular pattern includes a plurality of differing maximum vacuum peaks in the pattern.

10. The method of claim 6 wherein the non-regular pattern has irregularities during pressure application, where said irregularities are the occurrence of said pauses between plural consecutive cycles and one or more of: differing maximum pressure peaks; differing baseline vacuum levels; non-smooth curves; differing curve frequencies and operating the source of pressure according to this program.

11. The method of claim 10 wherein said pattern with irregularities repeats itself throughout a pumping session.

12. The method of claim 10 wherein the source of pressure is a source of vacuum.

13. The method of claim 6 wherein said non-regular pattern repeats itself throughout a pumping session.

14. The method of claim 6 wherein the source of pressure is a source of vacuum.

15. An electrically operated breastpump comprising:
a breastshield having a portion within which a woman's breast and nipple are received for expressing milk;
a source of pressure in communication with said breastshield for manipulating the breast and nipple to express milk;
a controller for operating the source of pressure according to sequences that yield a pattern of pumping cycles; and
a mechanism which automatically adjusts the pattern of pumping cycles with random irregularities;
wherein the pattern comprises the occurrence of a pause to be determined by a random generator at random intervals in the pattern.

16. A method for breastpumping comprising:
providing a breastshield having a portion within which a woman's breast is received for expressing milk;
providing a source of pressure in communication with the breastshield which is operated by a controller;
operating the controller to operate the source of pressure in a manner to express milk by using a pattern of cycles; and
providing a mechanism which automatically adjusts the pattern of pumping cycles with random irregularities;
wherein the pattern comprises the occurrence of a pause to be determined by a random generator at random intervals in the pattern.

17. An improved method for operating a motor-driven breastpump having a source of pressure which is applied to a breast and nipple for expressing milk, wherein the improvement comprises:
operating the source of pressure in a pattern of pumping cycles,
providing a mechanism which automatically adjusts the pattern of pumping cycles with random irregularities during pressure application, where said irregularities include pauses between plural consecutive cycles, said pauses being determined by a random generator at random intervals in the pattern.

18. The method of claim 17, wherein said irregularities are further one or more of: differing maximum pressure peaks; differing baseline vacuum levels; non-smooth curves; and differing curve frequencies.

\* \* \* \* \*